United States Patent [19]

Finch

[11] 4,238,371

[45] Dec. 9, 1980

[54] METHANATION CATALYST

[75] Inventor: Jack N. Finch, Bartlesville, Okla.

[73] Assignee: Phillips Petroleum Company, Bartlesville, Okla.

[21] Appl. No.: 31,090

[22] Filed: Apr. 18, 1979

Related U.S. Application Data

[62] Division of Ser. No. 893,365, Apr. 4, 1978, Pat. No. 4,168,276.

[51] Int. Cl.$^3$ ............... B01J 21/04; B01J 21/08; B01J 23/28; B01J 23/72
[52] U.S. Cl. ............... 252/465; 252/443; 252/447; 252/455 R; 252/458; 252/467; 252/468; 252/469
[58] Field of Search ............... 252/455 R, 458, 465, 252/467, 443, 447, 468, 469

[56] References Cited

U.S. PATENT DOCUMENTS

| | | | |
|---|---|---|---|
| 2,990,427 | 6/1961 | Caldwell | 252/467 X |
| 3,361,535 | 1/1968 | Pollitzer et al. | 260/449 M |
| 3,595,920 | 7/1971 | Ellis et al. | 252/465 X |
| 3,631,104 | 12/1971 | Habermann et al. | 252/467 X |
| 3,962,140 | 6/1976 | Alcorn et al. | 252/470 |

*Primary Examiner*—W. J. Shine

[57] ABSTRACT

A copper-molybdenum composition and process for using the composition in the production of methane from mixtures of carbon monoxide and hydrogen.

10 Claims, No Drawings

METHANATION CATALYST

This application is a division of copending application Ser. No. 893,365 filed Apr. 4, 1978, now U.S. Pat. No. 4,168,276.

This invention relates to the production of methane. In one aspect this invention relates to a composition suitable for providing an improved catalyst system for the production of methane. In another aspect this invention relates to an improved process for producing methane from mixtures of carbon monoxide and hydrogen.

It has been known for some time that certain metals are effective in catalyzing the conversion of mixtures of carbon monoxide and hydrogen into significant yields of methane. It is also known that gaseous products containing large amounts of carbon monoxide and hydrogen often result from such processes as the gasification of heavy petroleum residues. As the natural gas reserves decline, it becomes increasingly more important to find more practical and aconomical ways of maximizing the production of methane from such gases.

The production of methane by the catalytic hydrogenation of carbon oxides has been extensively studied since 1902, when the reaction was first reported. G. Alex Mills and Fred W. Steffgen, in a paper entitled "Catalytic Methanation", *Catalysis Reviews* 8(2), 159–210 (1973), state that the metals having the most significant methanation activity are ruthenium, nickel, cobalt, iron and molybdenum.

In order to have a practical and economic methanation process, it is desirable to employ a catalyst which has a long life and which will give a high selectivity toward methane production. Molybdenum has been recognized in the past as having excellent thermal stability and catalyst life when employed in methanation; however, it has substantially lower activity and selectivity toward methane than does nickel. Accordingly, there has been a need in the art for a means of improving the activity and selectivity of molybdenum methanation catalysts. An object of the present invention is to provide a molybdenum composition suitable for providing an improved molybdenum methanation catalyst.

Another object of the present invention is therefore to provide an improved molybdenum-containing methanation catalyst.

Another object of the present invention is to provide a novel highly active copper-molybdenum methanation catalyst.

Another object of the present invention is to provide a highly active supported copper-molybdenum methanation catalyst.

Still another object of the present invention is to provide an improved process for the conversion of carbon monoxide to methane employing a molybdenum-containing methanation catalyst.

Accordingly, in accordance with one embodiment of the present invention a composition is provided consisting essentially of at least one copper oxide and at least one molybdenum oxide wherein the atomic ratio of copper to molybdenum is in the range of 0.1/1 to 10/1.

In accordance with another embodiment of the present invention, a composition is provided which is suitable for an improved supported catalyst composition, the composition essentially of at least one copper oxide, at least one molybdenum oxide, and a catalyst support wherein the atomic ratio of copper to molybdenum is in the range of 0.1/1 to 10/1.

In accordance with still other embodiment of the present invention, there is provided a process for producing methane comprising reacting hydrogen and carbon monoxide under methanation conditions, in the presence of active catalysts prepared from the aforementioned composition.

The novel catalysts of the invention are based on molybdenum. It has been discovered that mixtures of certain amounts of copper oxide with molybdenum oxides when suitably reduced provide catalysts which are quite superior in activity and selectivity toward methane production than methanation catalysts consisting essentially of only molybdenum. In the invention catalysts the atomic ratio of copper to molybdenum, i.e., the ratio of the number of atoms of copper to the number of atoms of molybdenum, is in the range of 0.1/1 to 10/1, more preferably in the range of 1/1 to 5/1. In an especially preferred embodiment the ratio is about 2/1.

As with prior art molybdenum catalysts the present inventive molybdenum catalysts are much more active if they are employed in conjunction with a catalyst support. The term catalyst support as used herein is intended to include any inert carrier which may serve either as a diluent for particles of the essential ingredients of the catalyst or as a carrier upon which the essential ingredients of the catalyst are impregnated or otherwise deposited. Examples of typical catalyst supports include alumina, graphite, calcium titanate (perovskite), zirconia, pumice, silicon carbide, silica, and silica-alumina. The present preferred support is catalytic grade eta or gamma alumina, especially in the form of extrudates. In a commercial reaction, for economic reasons, it is generally desirable to use a catalyst support which may constitute from 50 percent to 99 percent, and preferably between 70 and 95 percent by weight of the finished catalyst.

Any of the oxides of copper and molybdenum are suitable for the instant invention. Of the molybdenum oxides including molybdenum dioxide, molybdenum trioxide, molybdenum pentaoxide, and molybdenum sesquioxide, the preferred oxide is molybdenum trioxide.

The oxide composition used in preparing the catalysts of the instant invention may be prepared by using any suitable technique generally known to provide such oxide compositions. For example, separately formed molybdenum oxides and copper oxides can be blended together, or other molybdenum and copper compounds capable of being oxidized can be combined and then oxidized. In any case generally the oxides of molybdenum and copper are prepared by oxidizing compounds of the respective metals that are oxidizable to the oxides.

An oxide composition suitable for preparing a supported inventive catalyst can be prepared, for example, by the direct combination of finely divided aluminum nitrate nonahydrate, cupric nitrate trihydrate, and ammonium heptamolybdate tetrahydrate; then heating to about 125° C. to release water of hydration to form a paste containing an intimate mixture of the components, then following with additional heating to at least 600° C. to remove water, decompose the nitrate, and volatilize ammonia to yield an oxide composition consisting essentially of molybdenum oxide, copper oxide, and alumina.

A preferred method of preparing an oxide composition suitable for making a supported active catalyst is to impregnate a catalytic grade of alumina with a solution containing suitable molybdenum and copper salts. Use of a single solution requires, of course, that the metal salts of the two metals be sufficiently compatible to remain in solution. A typical example is an aqueous solution of ammonium heptamolybdate containing cupric ions and sufficient ammonium hydroxide to keep the cupric ions in solution. The cupric ions may be added in any suitable form, for example, as cupric nitrate, cupric salts of organic acids such as cupric formate, cupric acetate, or cupric salicylate. Salts having sulfur- or halogen-containing anions may be used but are less desirable. After impregnation the composite is then dried at about 125° C., then calcined at about 500°–550° C. to convert the metals to their oxides. The process of impregnation may be repeated as needed to obtain the desired level of copper and molybdate.

A still more preferred method of preparing an oxide composition suitable for making a supported inventive catalyst is to impregnate a preformed molybdena-alumina catalyst with a suitable copper compound. The preformed molybdena-alumina catalyst may be made, for example, by impregnating catalytic grade alumina with aqueous ammonium heptamolybdate, drying at about 125° C., then calcining at about 500°–550° C., and repeating as needed to obtain the desired loading of molybdenum. This molybdena-alumina catalyst is then impregnated with a solution of a suitable copper compound. Aqueous cupric nitrate of cupric salts of organic acids such as cupric formate, cupric acetate, or cupric salicylate are suitable. Here again, although salts containing sulfur or halogen can be used, they are not preferred. Also, it is to be noted that any suitable solvent can be employed. Thus solvents such as ethanol may be used in place of water. The resulting impregnated composite is then dried at about 125° C. and then calcined at about 500°–550° C. to yield the oxide containing composition.

Thus in general the preparation of the oxide compositions involves either the admixing of the oxides or of suitable compounds which upon calcination will yield the oxides of copper and molybdenum.

Other variations in starting materials will suggest themselves to those skilled in the art, particularly where preferred starting materials mentioned above are unsuited to the economics of large-scale manufacture. In general, any compound containing the desired catalyst components may be used provided that it results, upon heating to a temperature within the range disclosed hereinafter, in a complex of oxides of the essential catalytic ingredients, which complex upon reduction yields the methanation catalyst of this invention.

The oxide compositions are converted to active methanation catalysts by contacting the composition with a reducing gas under conditions sufficient to provide sufficient reduction of the oxides in the oxide composition to result in a catalyts having methanation activity. Generally hydrogen is employed for reducing the oxides to produce an active catalyst. Generally, the reduction is carried out prior to contacting the material with the hydrogen and carbon monoxide reactant mixture. However, the gaseous reactant mixture of hydrogen and carbon monoxide can serve to reduce the oxides and produce an active catalyst. Generally, sufficient reduction can be achieved by heating the oxide composition in the presence of hydrogen in the temperature range of about 260° C. to about 530° C. for about 2 to about 24 hours, preferably about 450° C. to about 500° C. for about 2 hours.

The process of the instant invention is specifically concerned with the production of methane from carbon monoxide and hydrogen using as a catalyst a catalytic amount of the unsupported or supported inventive molybdenum-copper catalysts. Although the stoichiometric ratio of hydrogen to carbon monoxide is 3, reactants are not generally consumed in that ratio because some carbon monoxide is converted to carbon dioxide, to heavier hydrocarbons, and in some cases free carbon. Generally methanation can be carried out with the inventive catalysts for gaseous reactant mixtures having a hydrogen to carbon monoxide molar ratio in the range of about 1/1 to about 10/1. In a preferred embodiment, the ratio is in the range of about 2.8/1 to about 3.2/1.

The reaction temperatures employed in the practice of this inventive process can vary over a wide range but will generally fall within the range of about 300° to about 625° C. The preferred temperature range is from about 450° C. to about 550° C.

The pressure employed can also vary over a wide range but will generally fall within the range of about 0 to about 12000 psig (i.e., about 100 to about $83 \times 10^3$ kilopascals). Because there is a net decrease in reactant volume during the methanation process, pressures above atmospheric enhance the conversion. Thus, it is preferred that the process be conducted at a pressure in the range of about 100 to about 2000 psig (i.e., about $8 \times 10^2$ to about $1.4 \times 10^3$ kilopascals).

The contact time between the reactants and the catalyst can also vary widely. Generally the contact time, in terms of volumes of gas at STP (standard temperature and pressure) per volume of catalyst per hour is in the range of about 200 to about 10,000, preferably in the range of about 600 to about 5,000.

The following examples will further illustrate the present inventive catalyst and process.

Two different continuous flow reactors were used to make the tests that are described in the following examples. One, made of glass, was operated at atmospheric pressure. The other was made from stainless steel and was operated at 900 kilopascals (115 psig). Stoichiometric synthesis gas ($3H_2$:$1CO$) to both reactors was made by separately metering streams of hydrogen and carbon monoxide and combining them before they entered the reactor. For the atmospheric pressure studies in the glass reactor a feed rate of 52 cc/min STP was used; for the elevated pressure studies in the stainless steel reactor the rate was about 120 cc/min STP.

The catalysts were in the form of 16–60 mesh particles U.S. Series made by crushing and screening a commercial 11 percent $MoO_3$ on alumina (Harshaw's Mo 1202 T, surface area about 140 $m^2$ $gm^{-1}$) and impregnating with aqueous copper nitrate, then drying and calcining, to yield materials having various copper contents. The sole exception was the molybdenum-free catalyst that was made by impregnating catalytic grade alumina (Harshaw's Al 1404, surface area about 180 $m^2$ $gm^{-1}$) with copper nitrate.

Conversion data are presented using an expression simplified from a formula proposed by the Institute of Gas Technology (IGT, Research Bulletin No. 31, Chicago, July 1963) that expresses conversion of hydrogen and carbon monoxide to methane on an equal basis as:

Conversion = summarizes the results of tests on these five catalysts at 550° C.

TABLE II.

| | | METHANATION TESTS AT 550° C., 0 PSIG | | | | | | | | | |
|---|---|---|---|---|---|---|---|---|---|---|---|
| | Time on | Conversion | | | | Product composition, mole %* | | | | | |
| Catalyst | Stream, Hrs. | to CH$_4$, % | GHSV | O$_2$ | N$_2$ | H$_2$ | CO | CO$_2$ | C$_1$ | C$_2$ | C$_{3+}$ |
| A (Mo/Al) | 2.5 | 12.6 | 970 | 0.07 | 0.18 | 68.9 | 24.6 | 2.5 | 3.4 | 0.29 | 0 |
| B (Cu/Al) | 2 | 2.9 | 919 | 0.04 | 0.11 | 73.2 | 25.2 | 0.68 | 0.76 | 0 | 0 |
| C (Cu/Mo/Al) | 2 | 32.2 | 1037 | 0.05 | 0.18 | 67.7 | 14.8 | 6.3 | 10.7 | 0.28 | 0 |
| D (Cu/Mo/Al) | 1.5 | 39.6 | 1040 | 0.06 | 0.17 | 64.5 | 14.2 | 7.5 | 13.3 | 0.19 | 0 |
| E (Cu/Mo/Al) | 2 | 25.6 | 702 | 0.09 | 0.16 | 72.3 | 14.9 | 4.5 | 7.9 | 0.26 | 0 |

*Determined by gas liquid chromatography $$100 \left[ 4 \left( \frac{\text{Moles dry product gas}}{\text{Moles dry synthesis gas}} \right) \left( \text{Mole fraction of CH}_4 \text{ in dry product gas} \right) \right]$$

EXAMPLE I

Five catalysts that were prepared using the techniques and materials discussed above were tested under identical conditions. They are described in Table I.

TABLE I.

| | DESCRIPTION OF CATALYSTS | | | |
|---|---|---|---|---|
| Catalyst | Source | Impregnant | Calculated Concentration of Cu in Catalyst, wt. % | Atomic ratio, Cu/Mo |
| A | 11% MoO$_3$/Al$_2$O$_3$ | None | 0 | None |
| B | Catalytic Al$_2$O$_3$ | Cu(NO$_3$)$_2$ | 5.02 | None |
| C | 11% MoO$_3$/Al$_2$O$_3$ | Cu(NO$_3$)$_2$ | 4.76 | 1.03 |
| D | 11% MoO$_3$/Al$_2$O$_3$ | Cu(NO$_3$)$_2$ | 9.88 | 2.26 |
| E | 11% MoO$_3$/Al$_2$O$_3$ | Cu(NO$_3$)$_2$ | 24.0 | 6.49 |

The concentration of copper in the catalyst shown in the preceding table is the calculated quantity in the dry catalyst if all the added copper nitrate were reduced to elemental copper, the alumina and molybdenum trioxide (if present), being unaltered. In other words, the weight percent copper is the number of grams of copper added to each 100 grams of alumina and molybdenum trioxide (if present).

Each catalyst was tested individually by charging to the glass reactor, heating under flowing hydrogen for two hours at 500° C., then beginning the test of methanation activity by feeding synthesis gas as described above. Measurements of the conversion of synthesis gas were made at various, increasing temperatures. Table II Results in Table II, obtained at an identical temperature and at quite similar space rates, clearly show significant differences between the catalysts. Catalyst A, a standard molybdenum on alumina, showed only fair activity at 550° C. with 12.6 percent conversion. And Catalyst B, having copper only on alumina, produced only 2.9 percent conversion. However, Catalysts C, D and E, all illustrating compositions of this invention, showed substantially larger conversions of 32.3, 39.6 and 25.6 percent respectively for a series of increasing copper content. They indicate that Catalyst D, having a copper:molybdenum atomic ratio slightly greater than two, is the preferred composition of the three inventive catalysts tested.

EXAMPLE II

The catalysts identified as A and D in Table I of Example I were also compared for methanation activity over a range of temperatures at elevated pressure—900 kilopascals—in the stainless steel reactor. The two catalysts, tested separately, were heated at 500° C. for two hours in flowing hydrogen before they were cooled at 300° C. and synthesis gas was introduced for measurement of methanation activity. Table III summarizes results with these two catalysts.

TABLE III.

| COMPARISON OF METHANATION ACTIVITY OF MOLYBDENUM/ ALUMINA WITH AND WITHOUT ADDED COPPER | | | | | | | | | | | |
|---|---|---|---|---|---|---|---|---|---|---|---|
| | | | Conversion | | | | Product composition, mole %* | | | | |
| Catalyst | Temp., °C. | stream, hrs. | to CH$_4$, % | O$_2$ | N$_2$ | H$_2$ | CO | CO$_2$ | C$_1$ | C$_2$ | C$_{3+}$ |
| A | 300 | 1 | 0.3 | 0.19 | 0.35 | 78.8 | 20.5 | 0.08 | 0.07 | 0 | 0 |
| A | 350 | 1.5 | 0.8 | 0.15 | 0.23 | 77.5 | 21.6 | 0.26 | 0.21 | 0.04 | 0 |
| A | 400 | 2 | 3.3 | 0.17 | 0.23 | 77.2 | 20.4 | 0.89 | 0.86 | 0.13 | 0.04 |
| A | 450 | 2.5 | 8.7 | 0.15 | 0.24 | 76.5 | 18.2 | 2.1 | 2.4 | 0.24 | 0.06 |
| A | 500 | 3 | 14.3 | 0.16 | 0.25 | 75.2 | 16.5 | 3.3 | 4.2 | 0.35 | 0.07 |
| A | 550 | 3.5 | 19.6 | 0.17 | 0.25 | 73.6 | 14.5 | 4.2 | 6.6 | 0.56 | 0.08 |
| D | 300 | 0.5 | 5.2 | 0.05 | 0.06 | 77.9 | 17.6 | 2.6 | 1.45 | 0.31 | 0.12 |
| D | 350 | 1 | 13.3 | 0.05 | 0.08 | 75.6 | 13.2 | 5.5 | 4.4 | 0.94 | 0.26 |
| D | 400 | 1.5 | 24.5 | 0.05 | 0.08 | 72.4 | 7.7 | 8.9 | 9.0 | 1.5 | 0.35 |
| D | 450 | 2 | 29.9 | 0.05 | 0.09 | 70.7 | 6.9 | 8.8 | 11.5 | 1.7 | 0.31 |
| D | 500 | 2.5 | 37.4 | 0.05 | 0.06 | 67.8 | 6.3 | 8.5 | 15.3 | 1.7 | 0.25 |
| D | 550 | 3 | 44.2 | 0.05 | 0.06 | 65.6 | 6.1 | 8.0 | 18.4 | 1.6 | 0.20 |

GHSV = 1088 during test of catalyst A
GHSV = 1327 during test of catalyst D
*Determined by gas liguid chromatography Methanation activity of catalyst A, a standard molybdenum on alumina increased from 0.3 to 19.6 percent conversion to methane as temperature was raised from 300° to 550° C. In marked contrast, inventive catalyst D, derived from catalyst A by the addition of copper, exhibited conversion to methane from 5.2 to 44.2 percent over the same temperature range, despite a modest increase in space rate. Thus, by the addition of copper which by itself was shown to have only slight activity for methanation, the activity of supported molybdenum to methanate synthesis gas has more than doubled.

From the foregoing description and illustrative examples, one skilled in the art can easily ascertain the essential characteristics of this invention and without departing from the scope and spirit thereof, can make various changes and modifications to adapt the invention to various usages and conditions. Consequently such obvious changes and modifications should be within the range of equivalence of the following claims.

What is claimed is:

1. A methanation catalyst produced by impregnating a catalyst support with a solution of at least one oxidizable molybdenum compound, oxidizing the thus impregnated catalyst support to oxidize said at least one molybdenum compound, then impregnating the molybdenum oxide-containing support with a solution of at least one oxidizable copper compound and oxidizing the thus impregnated support to oxidize the said at least one copper compound, and then subjecting the resulting oxide composition to sufficient reduction to result in a catalyst having methanation activity, wherein said molybdenum and copper compounds are employed in such amounts that the atomic ratio of copper to molybdenum is in the range of 0.1/1 to 10/1.

2. A methanation catalyst according to claim 1 wherein said catalyst support is impregnated with aqueous solution of ammonium heptamolybdate, then the thus impregnated support is calcined to convert the ammonium heptamolybdate to molybdenum oxide, then the molybdenum oxide-containing support is impregnated with aqueous solution of cupric nitrate, and then the thus impregnated support is calcined to oxidize the cupric nitrate to copper oxide.

3. A methanation catalyst according to claim 2 wherein said catalyst support is selected from the group consisting of alumina, graphite, calcium titanate, zirconia, pumice, silicon carbide, silica, and silica-alumina.

4. A methanation catalyst according to claim 2 wherein said catalyst support is alumina.

5. A methanation catalyst according to claim 4 wherein the atomic ratio of copper to molybdenum is in the range of 1/1 to 5/1.

6. A methanation catalyst according to claim 4 wherein the atomic ratio of copper to molybdenum is about 2/1.

7. A methanation catalyst according to claim 4 wherein the molybdenum oxide-containing alumina contains 11 percent molybdenum oxide.

8. A methanation catalyst according to claim 7 wherein said cupric nitrate is employed in such an amount that the amount of copper therein equals about 5 weight percent of the weight of the molybdenum oxide-containing alumina.

9. A methanation catalyst according to claim 7 wherein said cupric nitrate is employed in such an amount that the amount of copper therein equals about 10 weight percent of the weight of the molybdenum oxide-containing alumina.

10. A methanation catalyst according to claim 7 wherein said cupric nitrate is employed in such an amount that the amount of copper therein equals about 24 weight percent of the weight of the molybdenum oxide-containing alumina.

* * * * *